(12) United States Patent
Moseley et al.

(10) Patent No.: US 12,702,444 B2
(45) Date of Patent: Aug. 11, 2026

(54) REDUCTION SYSTEM FOR SPONDYLOLISTHESIS

(71) Applicant: Spinal Simplicity, LLC, Overland Park, KS (US)

(72) Inventors: Todd Moseley, Olathe, KS (US); Jeffrey David Lee, Prairie Village, KS (US); Melissa Frock, Lenexa, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 844 days.

(21) Appl. No.: 17/989,949

(22) Filed: Nov. 18, 2022

(65) Prior Publication Data

US 2023/0149046 A1 May 18, 2023

Related U.S. Application Data

(63) Continuation of application No. 17/525,464, filed on Nov. 12, 2021, now Pat. No. 11,529,173.

(51) Int. Cl.

*A61B 17/66* (2006.01)
*A61B 17/64* (2006.01)
*A61B 17/56* (2006.01)

(52) U.S. Cl.

CPC .......... *A61B 17/66* (2013.01); *A61B 17/6458* (2013.01); *A61B 17/6483* (2013.01); *A61B 2017/564* (2013.01)

(58) Field of Classification Search

CPC ... A61B 17/7074–7079; A61B 17/7086–7088; A61B 17/80–8004; A61B 17/808; A61B 17/8014–8019; A61B 17/66; A61B 17/6483; A61B 17/6458

See application file for complete search history.

(56) References Cited

U.S. PATENT DOCUMENTS

| | | | | |
|---|---|---|---|---|
| 4,611,581 A * | 9/1986 | Steffee | A61B 17/7007 | 606/313 |
| 2005/0021040 A1* | 1/2005 | Bertagnoli | A61B 17/708 | 606/90 |
| 2006/0084983 A1* | 4/2006 | Kim | A61B 17/7065 | 606/279 |
| 2010/0274298 A1* | 10/2010 | Schiff | A61B 17/861 | 606/86 A |

(Continued)

FOREIGN PATENT DOCUMENTS

| | | | |
|---|---|---|---|
| EP | 0602351 A1 * | 6/1994 | A61B 17/7077 |
| FR | 2932375 A1 * | 12/2009 | A61B 17/7059 |

(Continued)

*Primary Examiner* — Eduardo C Robert
*Assistant Examiner* — Michelle C Green
(74) *Attorney, Agent, or Firm* — Erise IP, P.A.

(57) ABSTRACT

A system and method for reducing spondylolisthesis. The system includes a bracket comprising a first opening and a second opening, a first and second rod, and a first and second knob. The system may be placed onto a patient's back, the rods may be inserted through the first opening and the second opening and further into a first vertebral part and a second vertebral part. Tightening of a first knob and a second knob on the first and second rod allow for repositioning of the vertebra. Once repositioned, an interspinous implant may be inserted into the interspinous process space, connecting the vertebrae.

20 Claims, 5 Drawing Sheets

(56) References Cited

U.S. PATENT DOCUMENTS

| | | | | |
|---|---|---|---|---|
| 2010/0298885 | A1* | 11/2010 | Tribus | A61B 17/7077 606/279 |
| 2011/0106082 | A1* | 5/2011 | Kave | A61B 17/708 606/86 A |
| 2012/0053698 | A1* | 3/2012 | Huff | A61F 2/4637 29/700 |
| 2012/0310249 | A1* | 12/2012 | Seex | A61B 17/025 606/90 |
| 2013/0110113 | A1* | 5/2013 | Glazer | A61B 17/025 606/90 |
| 2015/0313585 | A1* | 11/2015 | Abidin | A61B 17/025 600/219 |
| 2017/0151001 | A1* | 6/2017 | Williams | A61B 17/7059 |

FOREIGN PATENT DOCUMENTS

| | | | | |
|---|---|---|---|---|
| JP | 09187465 A | * | 7/1997 | A61B 17/60 |
| WO | WO-9426190 A1 | * | 11/1994 | A61B 17/7091 |

* cited by examiner

REDUCTION SYSTEM FOR SPONDYLOLISTHESIS

CROSS-REFERENCE TO RELATED APPLICATIONS

This patent application is a continuation application claiming priority benefit, with regard to all common subject matter, of U.S. patent application Ser. No. 17/525,464, filed Nov. 12, 2021, and entitled "REDUCTION SYSTEM FOR SPONDYLOLISTHESIS." The above-referenced application is hereby incorporated by reference in its entirety into the present application.

TECHNICAL FIELD

Embodiments of the invention generally relate to a system and method for treating a spinal condition. More specifically, embodiments of the invention relate to systems and methods for spondylolisthesis reduction.

RELATED ART

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal.

Over time, at birth, or due to injury, two vertebrae within the spine may become displaced against one another, resulting in a condition known as spondylolisthesis. Spondylolisthesis typically refers to a first vertebra that is displaced anteriorly against a second vertebra, while retrolisthesis refers to the first vertebra displacing posteriorly against the second vertebra. Typically, spondylolisthesis occurs in the lumbar spine at the L5-S1 level where the L5 vertebra displaces forward over the S1 vertebra. Spondylolisthesis can also occur between other vertebrae, such as, for example, between the L4 and L5 vertebrae, between the L3 and L4 vertebrae, or via the hangman's fracture wherein the C2 vertebra displaces anteriorly relative to the C3 vertebra due to the fracturing of the C2 vertebra's pedicles.

The posterior portion of a vertebra consists of eleven vertebral parts, including two pedicles, two laminae, and seven processes. One pedicle and one lamina are present on each side of the spinal cord. The seven processes consist of one spinous process, two transverse processes, and four articular processes. The spinous process extends posteriorly from the vertebra. The two transverse processes are on opposing sides of the vertebra and project laterally at the point where the lamina meets the pedicle. The articular processes extend from the junctions of the pedicles and the laminae and can be categorized into superior articular processes that extend upwards and inferior articular processes that extend downwards, with one super articular process and one inferior articular process on each side of the spinal cord. The superior articular process from one vertebra connects to the interior articular processes from the vertebra directly above.

Various methods have been developed to treat spondylolisthesis. Often patients are instructed to perform non-operative treatments such as physical therapy, exercise, and bracing to relieve pain or discomfort. Medication such as nonsteroidal anti-inflammatories, analgesics, and steroids may also be used. When spondylolisthesis becomes severe, operative treatments may be required to correct the vertebra slippage. Traditional surgical approaches typically involve open surgeries with direct decompression and instrumented fusion of the spine. Such surgeries include anterior, posterior, or transforaminal lumbar interbody fusion. When treating spondylolisthesis, open surgery may lead to the destabilization of surrounding bony support structures, such as the facet joints of the spine. Percutaneous or minimally invasive processes have become a popular alternative over open surgery for treating spondylolisthesis and can reduce surgical trauma, postoperative complications, and hospital stay that may occur as a result of open surgery. Lumbar interbody fusion surgeries may also be performed using minimally invasive techniques.

Spondylolisthesis correction typically involves spinal fusion of the two vertebrae afflicted by spondylolisthesis. Spinal fusion may involve an interspinous implant that allows for the fixation of the thoracic, lumbar, and sacral spine while waiting for bony fusion to occur. Examples of a particularly useful interspinous process implant and fusion devices are disclosed in commonly assigned U.S. Pat. Nos. 9,861,399, 8,945,184 ("the '184 Patent"), U.S. Pat. Nos. 9,314,276, 9,907,581, 9,757,164, and U.S. patent application Ser. No. 16/998,171, which was filed on Aug. 8, 2020, and is entitled 'INTERSPINOUS PROCESS IMPLANT', the disclosures of which are all incorporated herein by reference in their entirety.

SUMMARY

Embodiments of the invention address the above-identified need by providing systems and methods for spondylolisthesis reduction. A spondylolisthesis reduction system may comprise a bracket, rods, and knobs. The bracket may be placed on a patient's back. The rods may be inserted into corresponding openings in the bracket and further into the patient's back. A knob may be threaded onto each rod configured to pull the rods, thereby repositioning a vertebra to reduce spondylolisthesis. Once repositioned, a spinal implant may be inserted into the patient to promote spinal fusion.

A first embodiment is directed to a spondylolisthesis reduction system comprising: a first bracket configured to be placed onto the back of a patient, the first bracket comprising at least one opening; a first rod being received through the at least one opening, said first rod having a sharpened distal end configured to be inserted into a first vertebral part of a first vertebra; and a first knob having a first lumen therethrough, said first knob receiving the first rod through the first lumen. When said first knob is tightened onto the first rod, said first knob abuts the first bracket, pulls the first rod proximally, and is configured to reposition the first vertebra.

Another embodiment is directed to a spondylolisthesis reduction system comprising a bracket configured to be placed onto a patient, the bracket comprising a first opening and a second opening, a first rod configured to be inserted through the first opening and into a first vertebral part of a vertebra, a second rod configured to be inserted through the second opening and into a second vertebral part of the vertebra, a first knob configured to be tightened onto the first rod to pull the first rod, and a second knob configured to be tightened onto the second rod to pull the second rod. The pulling of at least one of the first rod or the second rod is configured to reposition the vertebra.

Another embodiment is directed to a method for spondylolisthesis reduction comprising placing a bracket onto a patient, the bracket comprising a first opening and a second opening, inserting a first rod through the first opening and into a first vertebral part of a vertebra, inserting a second rod through the second opening and into a second vertebral part of the vertebra, tightening a first knob onto the first rod to pull the first rod, and tightening a second knob onto the second rod to pull the second rod, and pulling at least one of the first rod and the second rod to reposition the vertebra.

Another embodiment is directed to a system for spondylolisthesis reduction comprising a first bracket configured to be placed onto a patient substantially over a first vertebral part of a vertebra, a second bracket configured to be placed onto a patient substantially over a second vertebral part of the vertebra, a first rod configured to be inserted through the first bracket and into the first vertebral part, a second rod configured to be inserted through the second bracket and into the second vertebral part, and a first knob configured to pull the first rod, a second knob configured to pull the second rod, wherein pulling at least one of the first rod and the second rod is configured to reposition the vertebra. In some embodiments, the system further includes an interspinous implant configured to be inserted into the patient after the vertebra has been repositioned.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
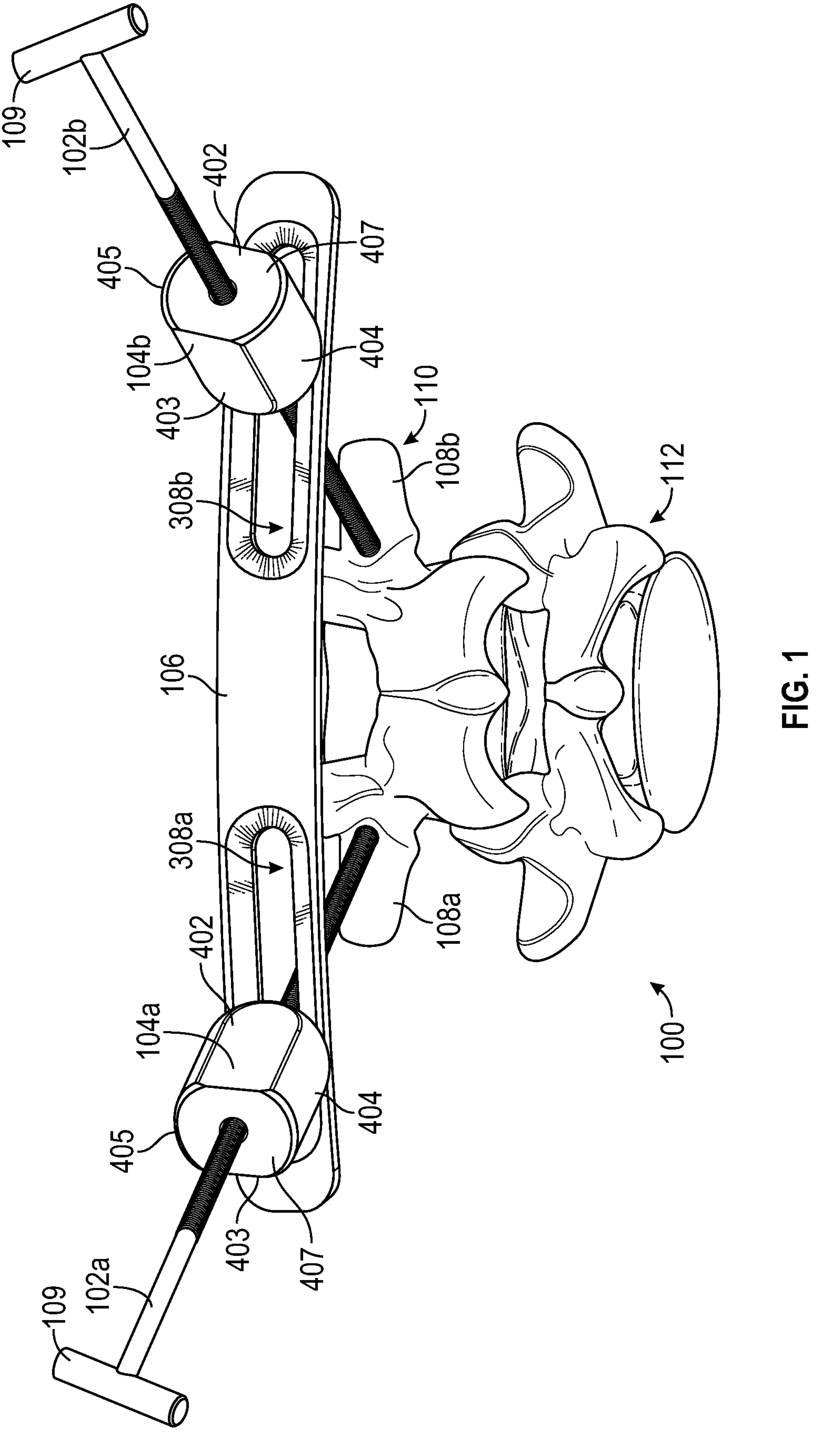
FIG. 1 illustrates a spondylolisthesis reduction system for certain embodiments.

The drawing figures do not limit the invention to the specific embodiments disclosed and described herein. The drawings are not necessarily to scale, emphasis instead being placed upon clearly illustrating the principles of the invention.

DETAILED DESCRIPTION

The subject matter of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claimed invention. Terms should not be interpreted as implying any particular ordering of various steps described unless the order of individual steps is explicitly described.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Embodiments are generally directed to a method and system for spondylolisthesis reduction. In some embodiments, the reduction system comprises a bracket placed substantially over a displaced vertebra. Two rods, each of which may be inserted into a vertebral part of the displaced vertebra, may be inserted through the bracket and into the vertebral parts. In some embodiments, the vertebral parts are on opposite sides of the spinal cord. The bracket may serve to keep the two rods substantially in place during the reduction procedure. A knob may be threaded onto each rod to pull the rods posteriorly, thereby repositioning the vertebra. Threading the knobs down the rods may create leverage against the bracket to facilitate the pulling of the rods and the repositioning of the vertebra. In some embodiments, the spondylolisthesis reduction process is performed posteriorly. In some embodiments, the displaced vertebra is repositioned to allow for an interspinous spinal implant to be inserted into the spine. Retrolisthesis may also be corrected using embodiments described herein.

FIG. 1 illustrates a reduction system 100 for treating spondylolisthesis for some embodiments. In some embodiments, reduction system 100 comprises a first rod 102*a*, a second rod 102*b*, a first knob 104*a*, a second knob 104*b*, and bracket 106. As described above, to facilitate spondylolisthesis reduction, first rod 102*a* may be inserted into first vertebral part 108*a* and second rod 102*b* may be inserted into second vertebral part 108*b*. In some embodiments, first vertebral part 108*a* and second vertebral part 108*b* are vertebral parts of first vertebra 110. In some embodiments, first vertebra 110 is the slipped or displaced vertebra causing spondylolisthesis. In some embodiments, vertebral parts 108*a*, 108*b* are one of the laminae, pedicles, or the transverse processes. Once rods 102*a*, 102*b* are in place, knobs 104*a*, 104*b* may then be translated down rods 102*a*, 102*b* via a rotational force, thus pulling rods 102*a*, 102*b* posteriorly from the patient and allowing first vertebra 110 to be repositioned. In some embodiments, the various components of reduction system 100 are interchangeable. For example, first rod 102*a* may be inserted into second vertebral part

108*b*, and second knob 104*b* may be threaded onto first rod 102*a* to reposition second vertebral part 108*b*.

To facilitate spondylolisthesis reduction using reduction system 100, bracket 106 may be arranged onto a patient's back prior to inserting rods 102*a*, 102*b* into the patient. Bracket 106 may be positioned on the patient substantially over the location of the first vertebra 110 that is to be repositioned. In some embodiments, imaging systems, such as fluoroscopy, three-dimensional imaging, computed tomography (CT) scanning, robotics, or any combination thereof, are utilized to aid in correctly positioning bracket 106 and other components of reduction system 100 described herein. Once bracket 106 is in place, rods 102*a*, 102*b* may be inserted through the patient's tissue and into the vertebral parts 108*a*, 108*b*. In some embodiments, rods 102*a*, 102*b* may be inserted into the patient before bracket 106 is placed onto the patient, and bracket 106 is then placed over rods 102*a*, 102*b*.

In some embodiments, bracket 106 is substantially rectangular with rounded ends and comprises openings 308*a*, 308*b* for receiving rods 102*a*, 102*b* therein. In some embodiments, bracket 106 has a width of about 10 mm to about 20 mm, or about 20 mm to about 30 mm. In some embodiments, bracket 106 has a thickness of about 10 mm to about 20 mm, or about 20 mm to about 30 mm. In some embodiments, bracket 106 has a length of about 190 mm to about 205 mm, or about 205 mm to about 220 mm. In some embodiments, bracket 106 is about 17 mm thick, about 17 mm wide, and about 202 mm long. In some embodiments, bracket 106 comprises a substantially similar width and thickness. In some embodiments, bracket 106 may be oval, circular, or rectangular, or have any other desired shape.

In some embodiments, when rods 102*a*, 102*b* are tightened, such as by threading knobs 104*a*, 104*b*, bracket 106 may be leveraged against the patient's back, thus allowing rods 102*a*, 102*b* to adjust and reposition first vertebra 110 to correct spondylolisthesis or another deformity. In some embodiments, bracket 106 may be curved, arched, concave, or otherwise formed such that bracket 106 is configured to substantial conform to the shape of the patient's back. In some embodiments, bracket 106 may have a curvature of about 20° to about 25°, about 25° to about 30°, or about 30° to about 35°. In some embodiments, the curvature for bracket 106 is about 27°. As will be discussed further below, in some embodiments, bracket 106 may be replaced by two brackets with a first bracket for receiving first rod 102*a* and a second bracket for receiving second rod 102*b*.

Figure 2:
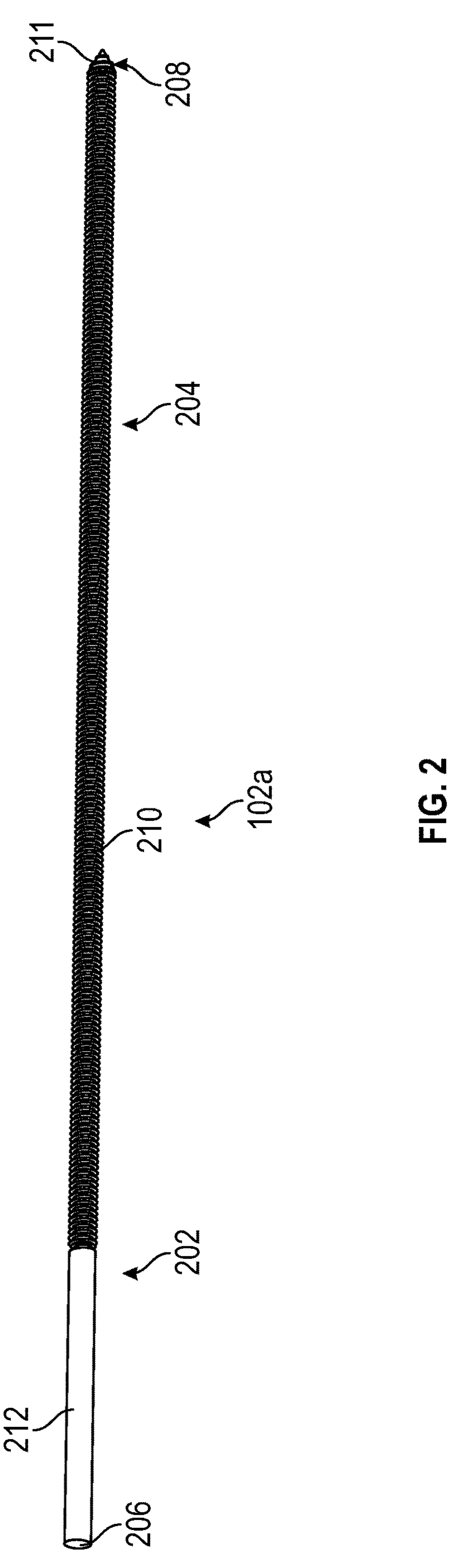
FIG. 2 illustrates a rod for use in the spondylolisthesis reduction system for certain embodiments.

In some embodiments, as seen in FIG. 2, rods 102*a*, 102*b* may be substantially cylindrical having a distal section 204 and a proximal section 202. During use, distal section 204 is configured to connect to vertebral parts 108*a*, 108*b* and a proximal section 202 is configured to remain outside of the patient's body. In some embodiments, rods 102*a*, 102*b* may have a circular, oval, rectangular, pentagonal, or hexagonal cross-sectional shape. In some embodiments, rods 102*a*, 102*b* may have any longitudinal form. In some embodiments, rods 102*a*, 102*b* may have a length of about 200 mm to about 250 mm, or about 250 mm to about 300 mm. In some embodiments, rods 102*a*, 102*b* may be about 250 mm in length. In some embodiments, rods 102*a*, 102*b* may have a diameter of about 2 mm to about 5 mm, or about 5 mm to about 8 mm. In some embodiments, rods 102*a*, 102*b* are about 5 mm in diameter. In embodiments where rods 102*a*, 102*b* are not cylindrical, rods 102*a*, 102*b* may be about 2 mm to about 8 mm wide at a widest point. In some embodiments, rods 102*a*, 102*b* may have a varying diameter or a varying cross-sectional area. In some embodiments, the diameter or cross-sectional area may be larger at the proximal end than at the distal end.

In some embodiments, rods 102*a*, 102*b* may be sanitized and/or sterilized prior to use to ensure no contaminants or bacteria are transferred to the patient. For example, rods 102*a*, 102*b* may be sterilized using standard surgical processes such as autoclaving, γ-irradiation, steam, ethylene oxide, hydrogen peroxide gas plasma, peracetic acid immersion, ozone sterilization techniques, or any combination thereof. Bracket 106 and knobs 104*a*, 104*b* may undergo similar sterilization procedures, either separately or together.

As described above, knobs 104*a*, 104*b* may be tightened onto rods 102*a*, 102*b* to pull rods 102*a*, 102*b* posteriorly, thus allowing first vertebra 110 to be repositioned. In some embodiments, knobs 104*a*, 104*b* may be substantially cylindrical in shape as shown, but include flat faces 402, 403 for enhancing gripping. In some embodiments, knobs 104*a*, 104*b* are substantially square, rectangular, spherical, or any other geometrical shape. As will be discussed further below with respect to FIG. 4A, knobs 104*a*, 104*b* may comprise a central lumen 410 for receiving a rod 102*a*, 102*b* therein. The lumen 410 may comprise internal threads 412 for cooperating with external threads 210 on rods 102*a*, 102*b*. Broadly, knobs 104*a*, 104*b* may take any geometric shape and comprise various dimensions provided that knobs 104*a*, 104*b* are capable of cooperating with rods 102*a*, 102*b* to pull 102*a*, 102*b* against bracket 106.

As described above, spondylolisthesis may occur between various adjacent vertebrae within the spine. In some embodiments, first vertebra 110 is considered to have "slipped" relative to a lower second vertebra 112. As described above, rods 102*a*, 102*b* may be inserted into the lamina, pedicle, transverse process, or other vertebral parts 108*a*, 108*b* of first vertebra 110. In some embodiments, first rod 102*a* is inserted into a different vertebral part than second rod 102*b*. For example, first rod 102*a* may be inserted into the lamina of first vertebra 110, while second rod 102*b* may be inserted into the pedicle of first vertebra 110.

In some embodiments, reduction system 100 is provided as a kit and packaged for surgical use. Each component of reduction system 100 is sterilized for single use or multiple uses. In some embodiments, at least a portion of reduction system 100 may be configured for reuse in the operating room, such as knobs 104*a*, 104*b* and/or bracket 106. In some embodiments, rods 102*a*, 102*b* are configured to be single use only. In some embodiments, reduction system 100 is entirely disposable and configured for single use only. Reduction system 100 may further comprise an interspinous implant that is inserted into the spine of the patient once reduction system 100 has repositioned first vertebra 110, as will be discussed in further detail below.

Turning now to FIG. 2, an exemplary first rod 102*a* is illustrated for certain embodiments. In some embodiments, rods 102*a*, 102*b* are substantially similar. In some embodiments, rods 102*a*, 102*b* may comprise various metals such as stainless steel, titanium, titanium alloys, steel, aluminum, aluminum alloys, or a combination thereof. In some embodiments, rods 102*a*, 102*b* comprise polymers such as acetal copolymer, polyether ether ketone (PEEK), polycarbonate, polypropylene, polyphenylsulfone, polytetrafluoroethylene (PTFE), polysulfone, polyphenylene sulfide, polyvinylidene fluoride, polyetherimide, polyphenylene oxide, or any combination thereof. In still other embodiments, rods 102*a*, 102*b* may comprise ceramics such as zirconia, bioglass, alumina, hydroxyapatite, or any combination thereof.

In some embodiments, first rod 102*a* comprises proximal section 202 and distal section 204. During use, distal section 204 is configured to contact first vertebral part 108*a* when first rod 102*a* is inserted into the patient. Proximal section 202 includes proximal end 206. In some embodiment, proximal end 206 may comprise a substantially flat face. In some embodiments, proximal end 206 is substantially blunt, spherical, conical, squared, rectangular, triangular, or any other geometrical shape. Proximal end 206 may be configured to attach to a handle 109, such as a quick connect handle, via a push-to-connect, a push-fit, or other similar connecting means. In some embodiments, proximal end 206 itself serves as the handle. In some embodiments, proximal end 206 may be formed to have a t-handle shape or a teardrop handle shape. In some embodiments, at least a portion of proximal end 206 is hollow to allow for the insertion of a handle therein. In some embodiments, the handle assists in inserting first rod 102*a* into the patient's back and further into first vertebral part 108*a*. The handle may be rotated, thus driving first rod 102*a* downwards. In some embodiments, the handle 109 may be a t-handle, a tear drop handle, a tapered handle, a ratchet handle, a crank handle, or any handle operable to rotationally drive first rod 102*a* into first vertebral part 108*a*. In some embodiments, first rod 102*a* is pushed into the patient and further into first vertebral part 108*a* via an axial force applied near proximal end 206. In some embodiments, once first rod 102*a* has been fully inserted into first vertebral part 108*a*, the handle (if present) may be removed from proximal end 206, and first knob 104*a* may be subsequently attached onto first rod 102*a*. In some embodiments, first knob 104*a* is already on the first rod 102*a* before the handle is attached, and the handle may remain in place throughout the operation.

Distal section 204 terminates in distal tip 208. In some embodiments, distal tip 208 may be a substantially sharp tip capable of being at least partially inserted into vertebral parts 108*a*, 108*b*. In some embodiments, distal tip 208 may include sharp threads 211 on an outer surface. In some embodiments, distal tip 208 is substantially conical or triangular. In some embodiments, prior to insertion of first rod 102*a*, a pilot hole is drilled into first vertebral part 108*a* for inserting distal tip 208 therein. In some embodiments, distal tip 208 is a self-drilling tip and comprises a drill-shaped point to cut through bone, thereby eliminating the need for drilling a pilot hole. In some embodiments, distal tip 208 may be removable from distal section 204 and may be interchanged with at least one other distal tip 208. For example, a self-drilling distal tip 208 may be replaced with a distal tip 208 configured for use with a pilot hole depending on the desired application. Removable distal tip 208 may be removably attached to the distal section 204 by a threaded interconnection or any other mechanical connection means.

In some embodiments, distal tip 208 comprises various features for enhancing attachment to first vertebral part 108*a*. For example, distal tip 208 may comprise threads, fangs, teeth, and/or hooks for attaching to first vertebral part 108*a*. In some embodiments, distal tip 208 may comprise a different material than proximal section 202 and/or distal section 204. For example, proximal section 202 and/or distal section 204 may comprise a polymer or a plastic and distal tip 208 may comprise a substantially hard metal capable of insertion into vertebral parts 108*a*, 108*b*.

In some embodiments, first rod 102*a* comprises external threads 210. As illustrated, external threads 210 may be present on the outer surface of at least a portion of first rod 102*a*. In some embodiments, external threads 210 may extend throughout the entirety of both proximal section 202 and distal section 204. In some embodiments, external threads 210 may extend partially into proximal section 202 and throughout distal section 204 up to distal tip 208, as illustrated in FIG. 2. As described above, in some embodiments, distal tip 208 may also comprise sharp threads 211. In some embodiments, sharp threads 211 on distal tip 208 are substantially identical to external threads 210. In some embodiments, external threads 210 are helical threads. In some embodiments, external threads 210 are alternatively or additionally box threads or cutter threads. In some embodiments, the external threads 210 may have a depth of about 0.25 mm to about 2.25 mm, an angle of about 45° to about 100°, and a spacing of about 0.25 mm to about 2.25 mm. In some embodiments, external threads 210 may have a depth of about 1.0 mm, an angle of about 60°, and a spacing of about 1.75 mm. External threads 210 may vary in depth, angle, spacing, or a combination thereof throughout the body of first rod 102*a*. For example, external threads 210 for distal section 204 may be coarser than those for distal tip 208.

Also present, in some embodiments, is non-threaded section 212 of first rod 102*a*. Non-threaded section 212 may reduce the lengths of first rod 102*a* that first knob 104*a* is threaded down. In some embodiments, proximal section 202 comprises at least a portion of non-threaded section 212 on the outer surface. In some embodiments, first rod 102*a* comprises external threads 210 along the length except for at distal tip 208. In some embodiments, first rod 102*a* comprises no external threads 210 and the outer surface is substantially smooth. In some embodiments, the entirety of the outer surface of first rod 102*a* comprises non-threaded section 212 except for distal tip 208 which may comprise sharp threads 211 or alternative cutting means.

Rod 102*b* may be substantially similar in any or all aspects to rod 102*a*. In some embodiments, rod 102*b* may have a different length, a different threading pattern, or a different distal tip 208 than rod 102*a*.

Figures 3A, 3B:
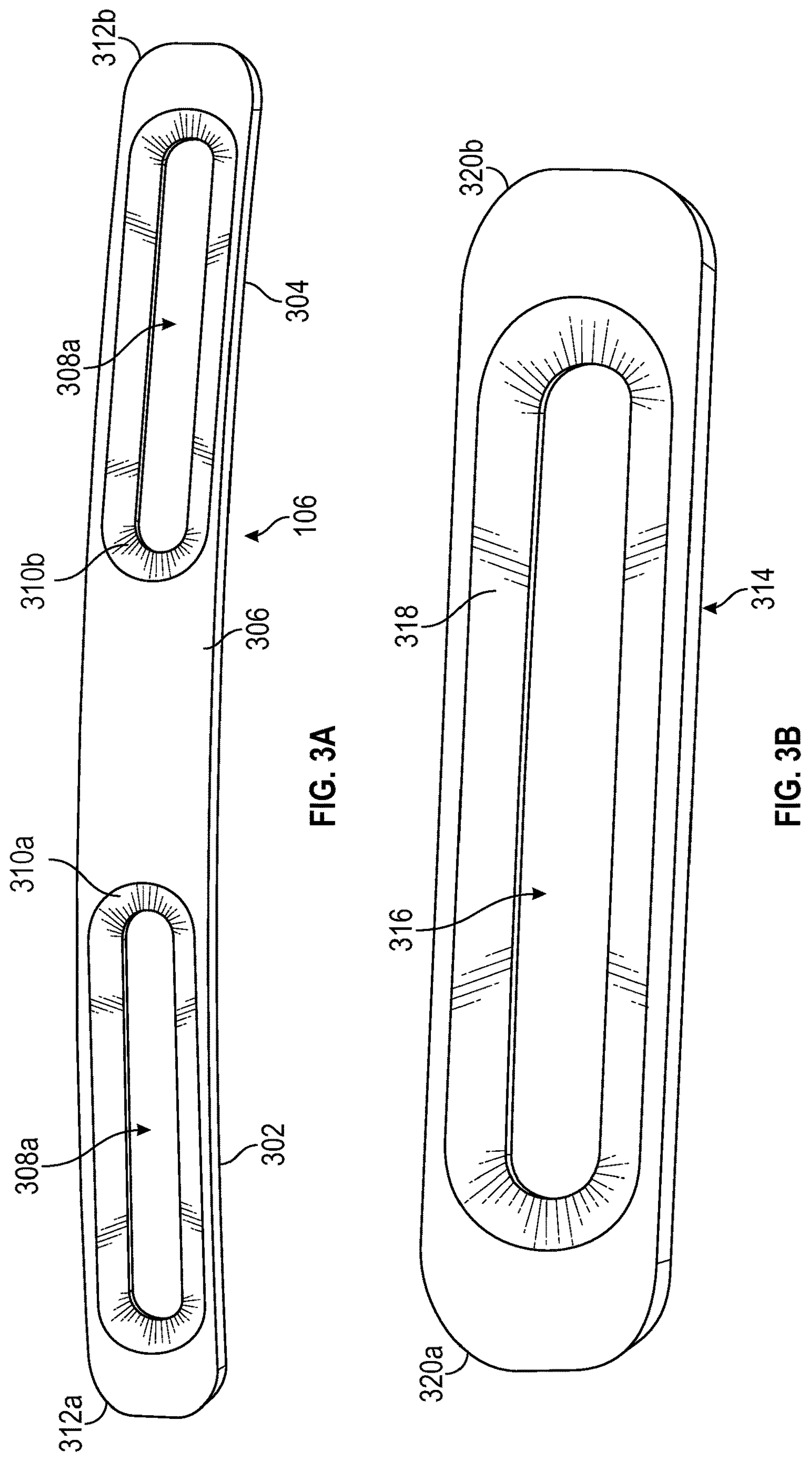
FIG. 3A illustrates a first embodiment of a bracket for use in the spondylolisthesis reduction system.
FIG. 3B illustrates a second embodiment of the bracket for use in the spondylolisthesis reduction system.

FIG. 3A illustrates exemplary bracket 106 for certain embodiments. Bracket 106 may comprise stainless steel, steel alloys, titanium, titanium alloys, aluminum, aluminum alloys, or any combination thereof. In some embodiments, bracket 106 comprises various polymers such as acetal copolymer, polyether ether ketone (PEEK), polycarbonate, polypropylene, polyphenylsulfone, polytetrafluoroethylene (PTFE), polysulfone, polyphenylene sulfide, polyvinylidene fluoride, polyetherimide, polyphenylene oxide, or any combination thereof. In some embodiments, the material for bracket 106 is selected such that bracket 106 is radiolucent and not visible when under fluoroscopy.

In some embodiments, bracket 106 comprises first section 302, second section 304, and third section 306, wherein third section 306 is disposed between first section 302 and second section 304. In some embodiments, first section 302 comprises first opening 308*a* for receiving first rod 102*a* therein, and second section 304 comprises second opening 308*b* for receiving second rod 102*b* therein. Openings 308*a*, 308*b* may be substantially similar to one another. In some embodiments, openings 308*a*, 308*b* are substantially oval, stadium-shaped, circular, or rectangular. As illustrated, openings 308*a*, 308*b* may comprise first chamfer 310*a* and second chamfer 310*b*, respectively. In some embodiments, chamfers 310*a*, 310*b* are substantially similar. In some embodiments, chamfers 310*a*, 310*b* are replaced with fillets having rounded edges. Openings 308*a*, 308*b* may comprise a length of about 15 mm to about 30 mm. In some embodiments, openings 308*a*, 308*b* comprise a width of about 5 mm to about 10 mm. In some embodiments, openings 308*a*, 308*b* comprise a length of about 25 mm and a width of about 8 mm. Openings 308*a*, 308*b* may be configured to substantially restrict the lateral and longitudinal movement of rods 102*a*, 102*b* and knobs 104*a*, 104*b* during use. As such, in some embodiments, there may be about 4 mm of clearance between the outer surface of first rod 102*a* and the inside walls of first chamfer 310*a* when first rod 102*a* is inserted through first opening 308*a*. Second rod 102*b*, second opening 308*b*, and second chamfer 310*b* may be similarly sized. Rods 102*a*, 102*b* may be configured to move laterally and longitudinally within openings 308*a*, 308*b* respectively to adjust the first vertebra 110. Knobs 104*a*, 104*b* may be sized such that they are larger than the openings 308*a*, 308*b*.

As described above and illustrated best with respect to FIG. 1, in some embodiments, bracket 106 is formed such that bracket 106 is shaped to fit the shape of the patient's back when the patient is lying face down on an operating table. Third section 306 may comprise a solid section of bracket 106 connecting first section 302 and second section 304. In some embodiments, third section 306 is about 45 mm to about 55 mm in length, or about 52 mm in length when measured from the rightmost part of first chamfer 310*a* on first section 302 to the leftmost part of second chamfer 310*b* on second section 304. In some embodiments, third section 306 may be omitted from bracket 106 and openings 308*a*, 308*b* are combined to form a single opening in bracket 106.

Bracket 106 may also comprise a first end 312*a* and a second end 312*b*. First end 312*a* and second end 312*b* may be substantially identical in some embodiments. In some embodiments, ends 312*a*, 312*b* are substantially round, circular, rectangular, or trapezoidal.

In some embodiments, bracket 106 is positioned onto the patient such that openings 308*a*, 308*b* are substantially above first vertebra 110 during use. In some embodiments, rods 102*a*, 102*b* are inserted into the patient substantially vertically. In some embodiments, rods 102*a* 102*b* are inserted into the patient at an angle of about 0° to about 30°, about 30° to about 60°, or about 60° to about 90° relative to the patient's back. During spondylolisthesis reduction, as knobs 104*a*, 104*b* are tightened and threaded down rods 102*a*, 102*b* towards the patient's back, knobs 104*a*, 104*b* may abut and press against bracket 106, thus providing leverage for repositioning first vertebra 110 and allowing rods 102*a*, 102*b* to pull first vertebra 110 from the slipped position.

FIG. 3B illustrates a second embodiment of bracket 106, referred to hereinafter as half bracket 314. As described above, in some embodiments, reduction system 100 may comprise two half brackets 314 rather than the single bracket 106 illustrated in FIGS. 1 and 3A. In embodiments in which reduction system comprises two half brackets 314, each of the two half brackets 314 may comprise a single opening 316 for receiving one of first rod 102*a* or second rod 102*b* therein. Opening 316 for half bracket 314 may be substantially similar to openings 308*a*, 308*b*. As such, one half bracket 314 may be configured to receive first rod 102*a* therein, and a second half bracket 314 may be configured to receive second rod 102*b* therein. Each of the half brackets 314 may be placed substantially above first vertebral part 108*a* and second vertebral part 108*b*, respectively. The positioning of half brackets 314 over vertebral parts 108*a*, 108*b* may be substantially similar to embodiments in which only single bracket 106 is utilized. In some embodiments, half brackets 314 comprise chamfers 318 which may be substantially similar to chamfers 310*a*, 310*b* for bracket 106. Half bracket 314 may also comprise a first end 320*a* and a second end 320*b*. In some embodiments, first end 320*a* and second end 320*b* are substantially similar. Ends 320*a*, 320*b* may be substantially round, circular, rectangular, or trapezoidal in some embodiments.

Figures 4A, 4B:
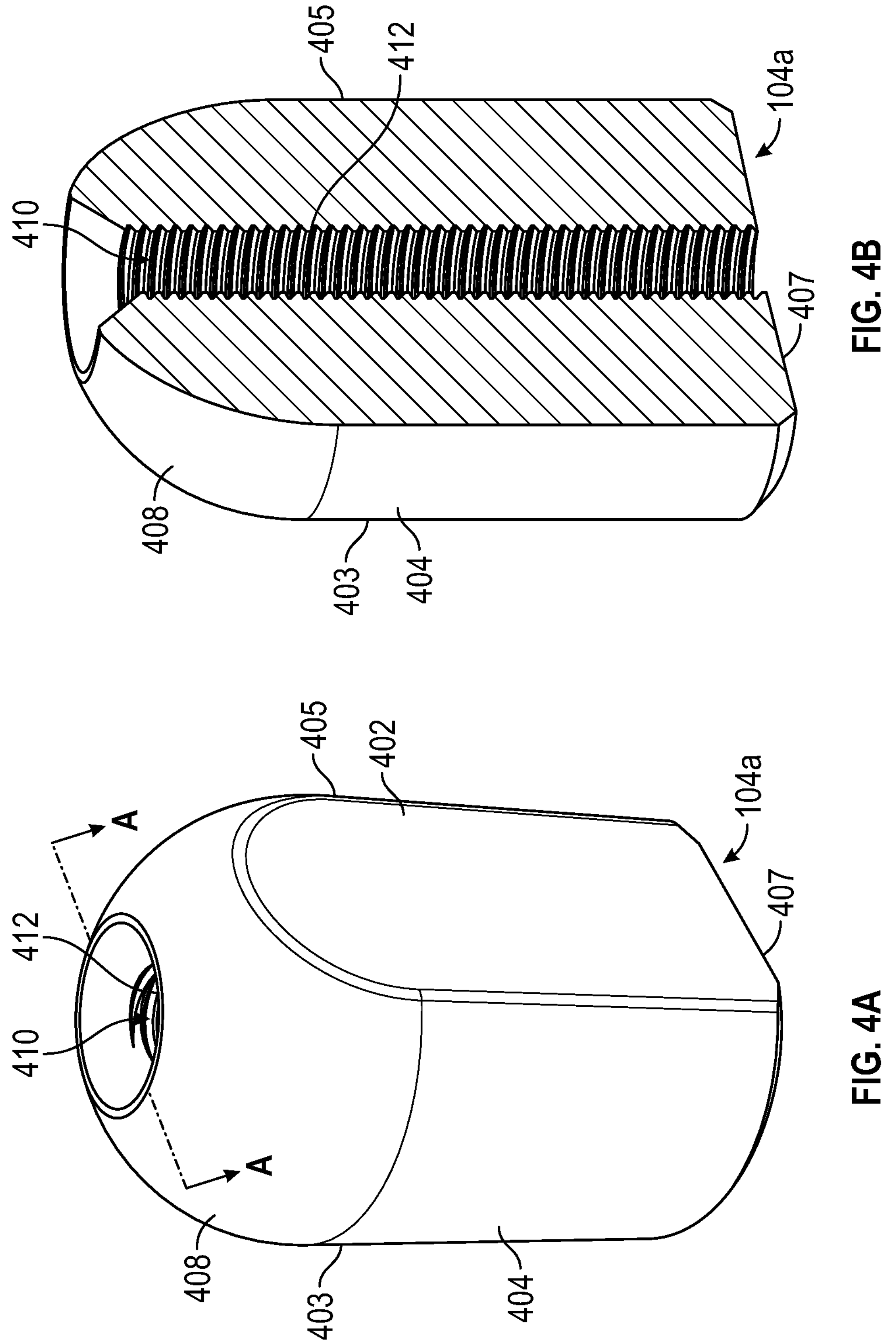
FIG. 4A illustrates a knob for use in the spondylolisthesis reduction system for certain embodiments.
FIG. 4B illustrates a cross-sectional view of the knob for certain embodiments.

FIG. 4A illustrates exemplary first knob 104*a* for some embodiments. In some embodiments, first knob 104*a* and second knob 104*b* may be substantially similar. As described above, first knob 104*a* may be threaded down the length of first rod 102*a* towards distal section 204. When first knob 104*a* contacts bracket 106, continually tightening first knob 104*a* may press bracket 106 into the patient's back, and first knob 104*a* may then pull first rod 102*a*, thus moving first vertebra 110.

As illustrated, first knob 104*a* comprises a substantially cylindrical shape with a first face 402 and a second face 404. In some embodiments, first face 402 is a substantially flat face and has an opposing flat face 403 on first knob 104*a*. In some embodiments, second face 404 comprises a substantially cylindrical face and has an opposing cylindrical face 405 on first knob 104*a*. In some embodiments, first knob 104*a* may be substantially symmetrical as best seen in FIG. 1. The geometry of first knob 104*a* may be configured to improve the ability of an operator to grip and thread first knob 104*a* down first rod 102*a*. In some embodiments, first knob 104*a* comprises a distal end 408 and a substantially flat proximal end 407 as seen best in FIG. 1. Broadly, knobs 104*a*, 104*b* may take any geometrical shape such as, spherical, cylindrical, rectangular, pentagonal, hexagonal, or any combination thereof. First knob 104*a* may also comprise a textured surface on any outer surface for finger placement to aid in gripping first knob 104*a*. As shown in FIG. 4A, the interfaces between first face 402, second face 404, distal end 408, the proximal end of first knob 104*a*, or any combination thereof may be chamfered or filleted to reduce the number of sharp edges present on first knob 104*a*.

As shown, distal end 408 may comprise a substantially domed shape. In some embodiments, distal end 408 comprises a substantially flat face or cylindrical face. Distal end 408 may comprise lumen 410 extending entirely through first knob 104*a*. In some embodiments, lumen 410 extends substantially through the center of first knob 104*a*. Lumen 410 may be substantially cylindrical and have a diameter of about 5 mm to about 15 mm. In some embodiments, lumen 410 comprises internal threads 412 on the inner surface. In some embodiments, internal threads 412 extend throughout the entirety of the inner surface of lumen 410. In some embodiments, internal threads 412 are configured to mate to external threads 210 on first rod 102*a*. In some embodiments, internal threads 412 are omitted, and the inner surface of lumen 410 is substantially smooth. As illustrated in FIG. 1, distal end 408 of first knob 104*a* may be threaded towards first vertebral part 108*a*. Distal end 408 may press against bracket 106 when first knob 104*a* is threaded distally down first rod 102*a*. In some embodiments, first knob 104*a* may instead be flipped during operation with the flat proximal face of first knob 104*a* pressing bracket 106 when first knob 104*a* is tightened.

First knob 104*a* may have a length of about 25 mm to about 35 mm, or about 35 mm to about 45 mm. In some embodiments, first knob 104*a* has a length of about 35 mm. In some embodiments, first knob 104*a* is about 10 mm to about 20 mm wide from first face 402 to the opposing flat face 403, or about 20 mm to about 50 mm wide from first face 402 to the opposing flat face 403. In some embodiments, second face 404 and the opposing curved face 405 are about 20 mm to about 50 mm in diameter, or about 25 mm in diameter. First knob 104*a* may comprise various materials. In some embodiments, first knob 104*a* comprises different materials than first rod 102*a* to reduce the occurrence of galling between external threads 210 and internal threads 412. First knob 104*a* may comprise a polymer, such as acetal copolymer, polyether ether ketone (PEEK), polyphenylsulfone, polytetrafluoroethylene (PTFE), polysulfone, polyphenylene sulfide, polyvinylidene fluoride, polyetherimide, polyphenylene oxide, or a combination thereof. In some embodiments, first knob 104*a* may comprise a plastic such that first knob 104*a* is radiolucent. Example plastic materials comprising first knob 104*a* include, but are not limited to, polyvinyl chloride, polycarbonate, polypropylene, polyethylene, or silicone.

In some embodiments, at least part of the outer surfaces of first knob 104*a* may be coated with a textured or grippable material and/or a sleeve comprising a textured or grippable material may be placed on an outer surface of first knob 104*a*. For example, a silicone or rubber sleeve may be added to a portion of first knob 104*a* to enhance an operator's ability to grip first knob 104*a*. In some embodiments, first knob 104*a* and/or the sleeve may further comprise various features to promote grip, such as ridges, bumps, knurling, checkered patterns, or any combination thereof. For example, first knob 104*a* may comprise a silicone sleeve covering faces 402, 403, 404, 405 while distal end 408 may be knurled to improve grip. FIG. 4B illustrates a cross section of first knob 104*a* cut along the A-A line illustrated in FIG. 4A. As shown, internal threads 412 may extend throughout the length of lumen 410, thus allowing first knob 104*a* to be threaded along the length of external threads 210.

Figure 5:
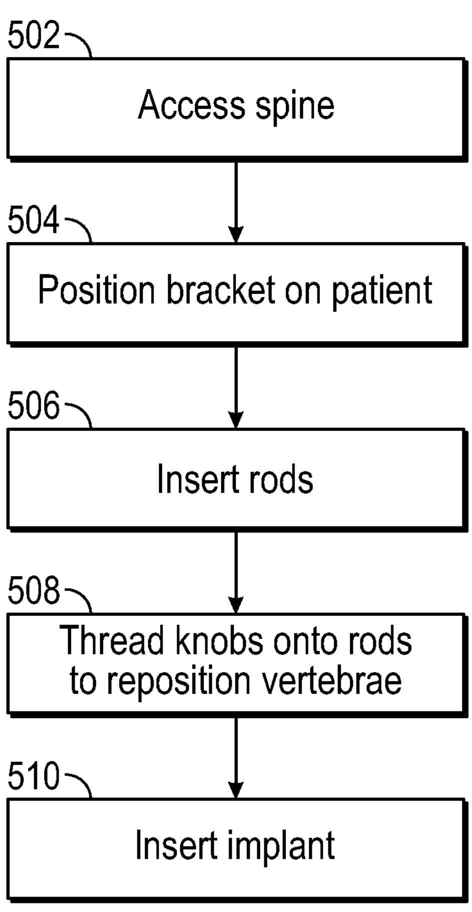
FIG. 5 illustrates an exemplary method for reducing spondylolisthesis for certain embodiments.

FIG. 5 illustrates an exemplary method 500 for spondylolisthesis reduction for some embodiments. The spondylolisthesis reduction may start at step 502 where the patient's spine may be accessed by the surgeon. As briefly described above, in some embodiments, spondylolisthesis reduction may be performed posteriorly with the patient lying on their stomach to allow the surgeon to access the spine posteriorly. The spine may be accessed using various techniques, such as minimally invasive techniques. In an example minimally invasive technique, a small incision may be made substantially above each of first vertebral part 108*a* and second vertebral part 108*b*. In some embodiments, a single minimally invasive incision is made to access both vertebral parts 108*a*, 108*b*. Once the incision has been made, a stylet or guidewire may be inserted through the incision to guide the surgeon in finding vertebral parts 108*a*, 108*b*. The stylet may form an entry path, along which one or more dilators may be sequentially advanced to dilate soft tissues between the incision and first vertebra 110. In some embodiments, a series of dilator sleeves may be placed over the guidewire, with each subsequent sleeve having a larger diameter than the previous sleeve. Once the one or more dilators have been inserted, the dilators may be removed, leaving the guidewire in place.

Adjacent spinal components and tissues may then be distracted using a distractor, such as a tap, that may be advanced to vertebral parts 108*a*, 108*b* following the dilation of the soft tissues. With the distractor in place in vertebral parts 108*a*, 108*b*, the guidewire may be removed. At least one sleeve may then be placed over the distractor, at which point the distractor may be removed from the patient, leaving the at least one sleeve in the patient's spine. The at least one sleeve may then be used to guide the surgeon in inserting rods 102*a*, 102*b*, leaving a clear pathway to vertebral parts 108*a*, 108*b*. The above-described minimally invasive technique may be performed via posterior access to first vertebra 110 and via lateral access to insert the interspinous implant. As described above, various internal imaging techniques, such as fluoroscopy, may be utilized to guide the surgeon throughout the reduction process. In some embodiments, the spine is accessed via an open surgical procedure. Broadly, any method of providing access to first vertebra 110 may be used for the embodiments described herein.

As described above, reduction system 100 may be used to reposition first vertebra 110, which may allow for the implantation of an interspinous implant. As such, in some embodiments, step 502 may also comprise an additional incision into the back or side of the patient to allow for the implantation of the interspinous implant. In some embodiments, the incision for inserting the interspinous implant is made after reduction system 100 is in place and first vertebra 110 has been repositioned. The above-described steps, including the guidewire, dilation, and distraction, for locating vertebral parts 108*a*, 108*b* may be followed for the additional incision as well. In some embodiments, the implant is inserted laterally. In some embodiments, rods 102*a*, 102*b* are inserted laterally and the implant is inserted posteriorly.

Next, at step 504, bracket 106 or half brackets 314 may be placed onto the patient's back with openings 308*a*, 308*b* placed substantially over the incisions, providing access for rods 102*a*, 102*b* to be inserted through openings 308*a*, 308*b*, into the incisions, and further into vertebral parts 108*a*, 108*b*. Once in place, brackets 106, 314 may be secured, such as via clamps, tape, Velcro, straps, or any combination thereof, to prevent brackets 106, 314 from moving during the procedure. In some embodiments, brackets 106, 314 are secured prior to inserting rods 102*a*, 102*b* therethrough. In some embodiments, brackets 106, 314 are secured after rods 102*a*, 102*b* are inserted into vertebral parts 108*a*, 108*b*.

At step 506, rods 102*a*, 102*b* may be inserted into the patient and further into the first vertebra 110 that need repositioning. As described above spondylolisthesis may occur at the L4-L5 vertebrae; as such, rods 102*a*, 102*b* may be placed into the L4 vertebra. Alternatively, rods 102*a*, 102*b* may be placed into the L5 vertebra if the slip is present between the L5-S1 vertebrae. Rods 102*a*, 102*b* may be placed into the laminae or pedicles of first vertebra 110 or any other part of first vertebra 110 such that rods 102*a*, 102*b* can be sufficiently inserted into vertebral parts 108*a*, 108*b*.

Rods 102*a*, 102*b* may be inserted into the patient's spine via a rotational or axial force as described above. In some embodiments, rods 102*a*, 102*b* are formed with a handle-shaped proximal end 206. In some embodiments, rods 102*a*, 102*b* are configured to attach to various handles, such as quick connect handles. In some embodiments, knobs 104*a*, 104*b* are placed onto rods 102*a*, 102*b* before attaching the handle. Alternatively, the handle may be used to insert rods 102*a*, 102*b* into vertebral parts 108*a*, 108*b*, and then the handle may be detached and knobs 104*a*, 104*b* placed onto rods 102*a*, 102*b*. In some embodiments, rods 102*a*, 102*b* are rotated into vertebral parts 108*a*, 108*b* by hand. Broadly, any method of inserting rods 102*a*, 102*b* into vertebral parts 108*a*, 108*b* is contemplated for embodiments herein.

At step 508, once rods 102*a*, 102*b* are in place and sufficiently attached to vertebral parts 108*a*, 108*b*, the repositioning of vertebral parts 108*a*, 108*b* may begin. As described above, knobs 104*a*, 104*b* may be tightened onto rods 102*a*, 102*b*. As knobs 104*a*, 104*b* are tightened, knobs 104*a*, 104*b* may contact brackets 106, 314. After making contact with brackets 106, 314, continually tightening knobs 104*a*, 104*b*, may press bracket 106 into the patient's back and leverage brackets 106, 314 against the patient's back. As such, as knobs 104*a*, 104*b* are continually tightened, rods

102*a*, 102*b* may be pulled posteriorly. Consequently, because rods 102*a*, 102*b* are attached to vertebral parts 108*a*, 108*b*, pulling vertebral parts 108*a*, 108*b* may move first vertebra 110. The surgeon may then continuously adjust knobs 104*a*, 104*b* to reposition first vertebra 110 to the desired position. Tightening knobs 104*a*, 104*b* may cause first vertebra 110 to further displace posteriorly, while loosening knobs 104*a*, 104*b* may cause first vertebra 110 to displace anteriorly. In some embodiments, only one of knobs 104*a*, 104*b* needs to be tightened to reposition first vertebra 110. For example, it may only be necessary to adjust first vertebra 110 by pulling on the right side lamina. As such, only one of rods 102*a*, 102*b* and one of knobs 104*a*, 104*b* may be utilized in reduction system 100.

In an alternative embodiment, knobs 104*a*, 104*b* are omitted from reduction system 100, such as when rods 102*a*, 102*b* are threadless. In such an embodiment, leverage may be applied to the bracket by an operator, and rods 102*a*, 102*b* may be pulled with a substantially axially force to reposition first vertebra 110.

At step 510, a spinal implant may be inserted into the spine. Reduction system 100, with first vertebra 110 in the new position, may be held in place while the implant is inserted. In some embodiments, the interspinous implant is inserted between first vertebra 110 and second vertebra 112 and attached at the spinous processes of each first vertebra 110 and second vertebra 112. As described above, the interspinous implant may be inserted laterally using a minimally invasive technique which may alleviate the need to dissect healthy tissue that occurs when performing open surgery. The interspinous implant may be injected with bone graft material to promote fusion. The bone graft may be either an autograft or an allograft. The volume of the bone graft material may range from about 0.5 cc to about 3.0 cc, or from 1.2 cc to about 2.5 cc, depending on the size of the interspinous implant. In some embodiments, the diameter of the interspinous implant may be about 8 mm, about 10 mm, about 12 mm, about 14 mm, or about 16 mm. In some embodiments, the interspinous implant is inserted between the two vertebrae affected by spondylolisthesis. For example, when spondylolisthesis occurs at the L4-L5 vertebrae, the implant may be inserted between the L4 and L5 vertebrae. Once implanted, the interspinous implant may work to fuse together first vertebra 110 and second vertebra 112.

As detailed in the ’184 Patent, the entirety of which is hereby incorporated by reference, the interspinous implant may comprise an elongated body dimensioned and configured to function as a spacer for placement in a target interspinous process space. In some embodiments, the interspinous process space is the space between two adjacent spinous processes. In some embodiments, the two adjacent spinous processes are the spinous processes of first vertebra 110 and second vertebra 112. The interspinous implant may comprise a distal anchor associated with a distal end of the implant body and a proximal anchor mounted for longitudinal movement along the body between a first position spaced apart from the head and a second position approximated with the head, adapted to compress the two adjacent spinous processes, in conjunction with the distal anchor.

Features described above as well as those claimed below may be combined in various ways without departing from the scope hereof. The following examples illustrate some possible, non-limiting combinations:

(A1) A spondylolisthesis reduction system comprising: a first bracket configured to be placed onto the back of a patient, the first bracket including at least one opening; a first rod being received through the at least one opening, the first rod having a sharpened distal end configured to be inserted into a first vertebral part of a first vertebra; and a first knob having a first lumen therethrough, the first knob receiving the first rod through the first lumen, wherein when the first knob is tightened onto the first rod, the first knob abuts the first bracket, pulls the first rod proximally, and is configured to reposition the first vertebra.

(A2) For the spondylolisthesis reduction system denoted as (A1), the at least one opening includes a first opening and a second opening, and wherein the first rod is received through the first opening, further including: a second rod being received through the second opening, the second rod having a sharpened distal end configured to be inserted into a second vertebral part of the first vertebra; and a second knob having a second lumen therethrough, the second knob receiving the second rod through the second lumen, wherein when the second knob is tightened onto the second rod, the second knob abuts the first bracket, pulls the second rod proximally, and is configured to reposition the first vertebra.

(A3) For the spondylolisthesis reduction system denoted as (A1) or (A2), the first knob includes internal threads in the first lumen and the first rod includes external threads, wherein the internal threads and the external threads cooperate together to tighten the first knob on the first rod.

(A4) For the spondylolisthesis reduction system denoted as (A2) or (A3), the second knob includes internal threads in the second lumen and the second rod includes external threads, wherein the internal threads and the external threads cooperate together to tighten the second knob on the second rod.

(A5) For the spondylolisthesis reduction system denoted as any of (A1) through (A4), the first rod has a proximal end, further including: a handle on the proximal end of the first rod, wherein the handle is configured to remain outside the patient during use and is configured to insert the sharpened distal end of the first rod into the first vertebral part when a rotational force is applied thereto.

(A6) For the spondylolisthesis reduction system denoted as any of (A2) through (A5), the second rod has a proximal end, further including: a handle on the proximal end of the second rod, wherein the handle is configured to remain outside the patient during use and is configured to insert the sharpened distal end of the second rod into the second vertebral part when a rotational force is applied thereto.

(A7) For the spondylolisthesis reduction system denoted as any of (A1) through (A6), the sharpened distal end of the first rod is removable.

(A8) For the spondylolisthesis reduction system denoted as any of (A2) through (A7), wherein the sharpened distal end of the second rod is removable.

(A9) For the spondylolisthesis reduction system denoted any of (A1) or (A3) through (A8), further including: a second bracket configured to be placed onto the back of the patient, the second bracket including at least one opening; a second rod being received through the at least one opening, the second rod having a sharpened distal end configured to be inserted into a second vertebral part of the first vertebra; a second knob having a second lumen therethrough, the second knob receiving the second rod through the second lumen, wherein when the second knob is tightened onto the second rod, the second knob abuts the second bracket, pulls the second rod proximally, and is configured to reposition the first vertebra.

(B1) A method for spondylolisthesis reduction in a patient comprising: providing posterior access to the spine of the patient; placing a first bracket onto the patient, the first bracket including at least one opening; providing a first rod having external threads and a sharpened distal end and a first knob having a first lumen therethrough having internal threads, inserting the first rod through the at least one opening and inserting the sharpened distal end into a first vertebral part of a first vertebra; tightening the first knob onto the external threads of first rod; and as the first knob abuts the first bracket, pulling the first rod proximally to reposition the first vertebra.

(B2) For the method denoted as (B1), further including: holding the repositioned first vertebra in place while an interspinous implant is inserted; and after the interspinous implant is implanted, removing the first rod from the patient.

(B3) For the method denoted as (B1) or (B2), wherein the at least one opening includes a first opening and a second opening, wherein the first rod is inserted into the first opening, further including: providing a second rod having external threads and a sharpened distal end and a second knob having a second lumen therethrough having internal threads, inserting the second rod through the second opening and inserting the sharpened distal end into a second vertebral part of the first vertebra; tightening the second knob onto the external threads of the second rod; and as the second knob abuts the first bracket, pulling the second rod proximally to reposition the first vertebra.

(B4) For the method denoted as (B3), further including: holding the repositioned first vertebra in place while an interspinous implant is inserted; and after the interspinous implant is implanted, removing the first rod and the second rod from the patient.

(B5) For the method denoted as any of (B1) through (B4), further including: placing a second bracket onto the patient, the second bracket including at least one opening; providing a second rod having external threads and a sharpened distal end and a second knob having a second lumen therethrough having internal threads, inserting the second rod through the at least one opening and inserting the sharpened distal end into a second vertebral part of the first vertebra; tightening the second knob onto the external threads of second rod; and as the second knob abuts the second bracket, pulling the second rod proximally to reposition the first vertebra.

(B6) For the method denoted as (B3) or (B5), further including: holding the repositioned first vertebra in place while an interspinous implant is inserted; and after the interspinous implant is implanted, removing the first rod and the second rod from the patient.

(C1) A system for spondylolisthesis reduction comprising: at least one bracket configured to be placed onto a patient substantially over at least a first vertebral part of a first vertebra; a first rod having a proximal end and a pointed distal tip; a second rod having a proximal end and a pointed distal tip; a first knob having an internally threaded lumen receiving the first rod therethrough; and a second knob having an internally threaded lumen receiving the second rod therethrough. The first rod can be inserted through the at least one bracket into the first vertebral part, the second rod can be inserted through the at least one bracket into a second vertebral part of the first vertebra, and pulling at least one of the first rod or the second rod is configured to reposition the first vertebra.

(C2) For the system denoted as (C1), the at least one bracket includes a first opening for receiving the first rod therethrough and a second opening for receiving the second rod therethrough.

(C3) For the system denoted as (C1) or (C2), the pointed distal tip of the first rod is a self-drilling tip configured to be inserted into bone.

(C4) For the system denoted as any of (C1) through (C3), the pointed distal tip of the second rod is a self-drilling tip configured to be inserted into bone.

(C5) For the system denoted as any of (C1) through (C4), the first knob has at least one flat face to facilitate gripping and wherein the second knob has at least one flat face to facilitate gripping.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and subcombinations and are contemplated within the scope of the claims. Although the invention has been described with reference to the embodiments illustrated in the attached drawing figures, it is noted that equivalents may be employed, and substitutions made herein, without departing from the scope of the invention as recited in the claims.

The invention claimed is:

1. A spondylolisthesis reduction system for repositioning a displaced vertebra, comprising:

a concave bracket configured to be placed onto an exterior back surface of a patient, the concave bracket having an opening therethrough;

a rod configured to be received through the opening, the rod having a distal end for insertion into the displaced vertebra;

a knob threadedly engaged with the rod, wherein when the knob is threaded down the rod towards the distal end, the knob abuts the concave bracket, thereby creating leverage against the exterior back surface to pull the rod posteriorly to reposition the displaced vertebra in a posterior direction; and an interspinous implant configured to be inserted when the displaced vertebra is repositioned.

2. The spondylolisthesis reduction system of claim 1, wherein the rod is a first rod, the knob is a first knob, the opening is a first opening and the concave bracket further comprises a second opening, and wherein the spondylolisthesis reduction system further comprises:

a second rod configured to be received through the second opening, the second rod having a second distal end for insertion into the displaced vertebra; and a second knob threadedly engaged with the second rod, wherein when the second knob is threaded down the rod towards the second distal end, the second knob abuts the concave bracket, thereby creating leverage to pull the second rod posteriorly to reposition the displaced vertebra.

3. The spondylolisthesis reduction system of claim 1, wherein the spondylolisthesis reduction system further comprises a handle that is removably attachable to a proximal end of the rod, wherein the handle is rotatable to insert the distal end into the displaced vertebra.

4. The spondylolisthesis reduction system of claim 1, wherein the distal end of the rod comprises a distal tip that is removable therefrom, and wherein the distal tip comprises at least one of: threads, teeth, fangs, or hooks for coupling to the displaced vertebra.

5. The spondylolisthesis reduction system of claim 1, wherein at least one of the knob or the concave bracket is formed from a radiolucent material.

6. The spondylolisthesis reduction system of claim 1, wherein the opening is configured to substantially restrict lateral movement and longitudinal movement of the rod.

7. The spondylolisthesis reduction system of claim 1, wherein the knob comprises at least one of a textured surface or a sleeve configured to enhance grip.

8. A spondylolisthesis reduction system for repositioning a displaced vertebra via a posterior approach, comprising:

a bracket configured to contact an external back surface of a patient, the bracket having an opening therethrough, wherein the bracket has a curvature configured to conform to a shape of the external back surface of the patient;

a rod configured to be inserted through the opening, the rod having a distal end for insertion into a vertebral part of the displaced vertebra; and a knob comprising a hole for receiving the rod, wherein when the knob is advanced down the rod towards the distal end, the knob abuts the bracket, thereby creating leverage against the external back surface to pull the rod posteriorly to move the displaced vertebra to a new position.

9. The spondylolisthesis reduction system of claim 8, wherein the rod is a first rod, the opening is a first opening, and the vertebral part is a first vertebral part, and wherein the spondylolisthesis reduction system further comprises a second rod configured to be inserted through a second opening of the bracket and further into a second vertebral part of the displaced vertebra.

10. The spondylolisthesis reduction system of claim 8, wherein the spondylolisthesis reduction system further comprises an interspinous implant for stabilizing the displaced vertebra.

11. The spondylolisthesis reduction system of claim 10, wherein the rod is configured to hold the displaced vertebra in the new position while the interspinous implant is inserted and configured to be removed from the patient after the insertion.

12. The spondylolisthesis reduction system of claim 8, wherein the hole comprises internal threads configured to cooperate with external threads on the rod, and wherein the external threads extend proximally from the distal end of the rod.

13. The spondylolisthesis reduction system of claim 12, wherein the knob comprises a material distinct from the rod to reduce galling between the internal threads and the external threads.

14. The spondylolisthesis reduction system of claim 8, wherein the bracket comprises a curvature of 20 to 25 degrees, 25 to 30 degrees, or 30 to 35 degrees.

15. A spondylolisthesis reduction system for repositioning a displaced vertebra, comprising:

a first curved bracket configured to be placed over a first vertebral part of the displaced vertebra, the first curved bracket comprising a first opening;

a second curved bracket configured to be placed over a second vertebral part of the displaced vertebra, the second curved bracket comprising a second opening enabling posterior access to the second vertebral part of the displaced vertebra, wherein the first curved bracket and the second curved bracket are configured to contact an external back surface of a patient;

a first rod configured to be received though the first opening, the first rod having a first distal end for insertion into the first vertebral part; and a second rod configured to be received through the second opening, the second rod having a second distal end for insertion into the second vertebral part, wherein pulling one of the first rod or the second rod posteriorly repositions the displaced vertebra.

16. The spondylolisthesis reduction system of claim 15, further comprising:

a first knob configured to be advanced along the first rod towards the first distal end, wherein when the first knob abuts the first curved bracket, the first knob provides leverage against the first curved bracket for pulling the first rod posteriorly.

17. The spondylolisthesis reduction system of claim 16, wherein the first rod includes external threads configured to cooperate with internal threads extending through a lumen of the first knob to advance the first knob towards the first distal end.

18. The spondylolisthesis reduction system of claim 16, further comprising:

a second knob configured to be advanced along the second rod towards the second distal end, wherein when the second knob abuts the second curved bracket, the second knob provides leverage against the second curved bracket for pulling the second rod posteriorly.

19. The spondylolisthesis reduction system of claim 18, wherein the second rod includes external threads configured to cooperate with internal threads extending through a lumen of the second knob to advance the second knob towards the second distal end.

20. The spondylolisthesis reduction system of claim 15, wherein the first vertebral part and the second vertebral part are on opposing sides of a spinal cord.

* * * * *